United States Patent
Katz et al.

[11] Patent Number: 5,879,716
[45] Date of Patent: Mar. 9, 1999

[54] METHODS AND COMPOSITIONS FOR TOPICAL DELIVERY OF BENZOYL PEROXIDE

[75] Inventors: Martin A. Katz, Menlo Park; Chung H. Cheng, San Jose; Sergio Nacht, Los Altos, all of Calif.

[73] Assignee: Advanced Polymer Systems, Inc., Redwood City, Calif.

[21] Appl. No.: 76,824

[22] Filed: Jun. 14, 1993

Related U.S. Application Data

[63] Continuation of Ser. No. 803,234, Dec. 5, 1991, abandoned, which is a continuation-in-part of Ser. No. 644,869, Jan. 23, 1991, Pat. No. 5,145,675, which is a continuation of Ser. No. 334,051, Apr. 5, 1989, which is a division of Ser. No. 91,641, Aug. 31, 1987, abandoned, which is a continuation-in-part of Ser. No. 810,478, Dec. 18, 1985, abandoned, Ser. No. 846,321, Mar. 31, 1986, abandoned, Ser. No. 896,956, Aug. 15, 1986, abandoned, Ser. No. 925,081, Oct. 30, 1986, abandoned, Ser. No. 925,082, Oct. 30, 1986, abandoned, Ser. No. 932,613, Nov. 20, 1986, abandoned, Ser. No. 933,243, Nov. 21, 1986, abandoned, Ser. No. 936,520, Dec. 1, 1986, abandoned, and Ser. No. 940,754, Dec. 10, 1986, abandoned.

[51] Int. Cl.$^6$ ..................................................... A61K 9/16
[52] U.S. Cl. ........................ 424/501; 514/951; 514/859
[58] Field of Search .......................... 424/78.31, 501; 514/951, 859

[56] References Cited

U.S. PATENT DOCUMENTS

| | | |
|---|---|---|
| 3,732,865 | 5/1973 | Higuchi et al. .......................... 424/455 |
| 3,758,686 | 9/1973 | Sieger et al. . |
| 4,221,871 | 9/1980 | Meitzner et al. . |
| 4,224,415 | 9/1980 | Meitzner et al. . |
| 4,282,216 | 8/1981 | Rovee et al. . |
| 4,321,117 | 3/1982 | Kaetsu et al. . |
| 4,427,793 | 1/1984 | Reed et al. . |
| 4,435,524 | 3/1984 | Dinbergs . |
| 4,477,467 | 10/1984 | Nishizawa et al. . |
| 4,478,818 | 10/1984 | Shell et al. . |
| 4,525,340 | 6/1985 | Lange et al. . |
| 4,542,069 | 9/1985 | Mauz et al. . |
| 4,548,990 | 10/1985 | Mueller et al. ........................ 526/332 |
| 4,590,068 | 5/1986 | Berthet et al. . |
| 4,690,825 | 9/1987 | Won . |
| 4,724,240 | 2/1988 | Abrutyn . |
| 4,734,286 | 3/1988 | Mahieu et al. .......................... 525/154 |

FOREIGN PATENT DOCUMENTS

| | | |
|---|---|---|
| 2692M | 7/1964 | France . |
| 2018589 | 10/1979 | United Kingdom . |
| 2156676 | 10/1985 | United Kingdom . |

*Primary Examiner*—Edward J. Webman
*Attorney, Agent, or Firm*—Heller Ehrman White & McAuliffe

[57] ABSTRACT

Benzoyl peroxide intended for topical application is incorporated in novel formulations in which it is retained as impregnants inside the pores of porous solid particles or microspheres. The pores form a continuous network open to the exterior of the particles, permitting outward diffusion of the benzoyl peroxide impregnant at a controlled rate depending on the pore size. The impregnated particles are prepared by impregnation of preformed particles with the benzoyl peroxide.

20 Claims, 3 Drawing Sheets

METHODS AND COMPOSITIONS FOR TOPICAL DELIVERY OF BENZOYL PEROXIDE

CROSS-REFERENCE TO RELATED APPLICATIONS

This is a Continuation of application Ser. No. 07/803,234 filed Dec. 5, 1991, now abandoned, which is a continuation-in-part of application Ser. No. 07/644,869, filed Jan. 23, 1991 now U.S. Pat. No. 5,145,675, which was a continuation of application Ser. No. 07/334,051 filed Apr. 5, 1989, which was a division of application Ser. No. 07/091,641, filed Aug. 31, 1987, now abandoned, which was a continuation-in-part of application Ser. No. 06/810,478, filed Dec. 18, 1985, now abandoned; Ser. No. 06/846,321, filed Mar. 31, 1986, now abandoned; Ser. No. 06/896,956, filed Aug. 15, 1986, now abandoned; Ser. No. 06/925,081, filed Oct. 30, 1986, now abandoned; Ser. No. 06/925,082, filed Oct. 30, 1986, now abandoned; Ser. No. 06/932,613, filed Nov. 20, 1986, now abandoned; Ser. No. 06/933,243, filed Nov. 21, 1986, now abandoned; Ser. No. 06/936,520, filed Dec. 1, 1986, now abandoned; and Ser. No. 06/940,754, filed Dec. 10, 1986, now abandoned. The full disclosures of each of these applications are incorporated herein by reference.

BACKGROUND OF THE INVENTION

The present invention relates to controlled release compositions comprised of porous polymeric microbead carriers retaining acne treatment substances within their pores. The invention further relates to methods of preparing such compositions and their methods of use.

Acne is a pleomorphic skin disease characterized by blackheads, whiteheads, papules, pustules, cysts, and various sized nodules and scars which, in the inflammatory stage of the disease, are contaminated with bacteria such as *Propionibacterium acnes*. The disease involves the pilosebaceous units of the dermis which consist of the sebaceous follicle which include the sebaceous glands and ducts and small hairs.

Sebum (skin oil) is a complex mixture of fats and waxes liberated by the breakdown of the sebaceous cells. The production of sebum is intimately associated with the pathology of acne. Obstruction of the opening of the sebaceous follicle forms a comedo, a solid horny mass or plug made up of keratinized cells and commonly referred to as whiteheads or blackheads, by blocking or stagnating sebum flow through the sebaceous follicle. This blockage may lead secondarily to rupture of the follicular contents (bacteria and sebum) into the dermis, and then to perfolliculitis. This provokes an inflammatory response which leads to the formation of pustules (pimples) when the rupture is small, and cystic nodules with complete rupture. A scar may eventually form, dependent on the depth and extent of the inflammatory response.

Benzoyl peroxide is an oxidizing agent believed to be one of the most effective topical nonprescription medications available for acne. Benzoyl peroxide is one of several topical agents used in treating acne to cause mild irritation and desquamation, thereby preventing closure of the pilosebaceous orifice. The irritant effect of benzoyl peroxide can cause an increased turnover rate of epithelial cells lining the follicular duct, which increases sloughing. The desired effect is to reduce the tendency of the skin to form new comedones and to loosen the structure of the formed comedones and aid in their extrusion. The primary action of benzoyl peroxide, however, is as a bactericide, but it is believed that the irritancy also has a beneficial effect, as described below.

In the past, benzoyl peroxide has been administered to the skin in the form of gels, creams, lotions or ointments in concentrations of 2.5%–5.0% and 10%. There are several disadvantages to prior methods of delivering benzoyl peroxide to affected areas. Strong concentrations of benzoyl peroxide cannot be used because high concentrations of the topical agent can cause localized reactions such as stinging and burning. Benzoyl peroxide is also a strong bleaching agent, and can permanently discolor sheets, pillowcases, towels, clothing or any other colored textiles if a liquid or gel containing the agent is spilled or otherwise contacts such articles.

A common problem with the use of benzoyl peroxide for the treatment of acne has been excessive skin irritation. Although a controlled irritation is believed to contribute to effectiveness, it would be desirable to reduce the side effects of irritancy without substantially reducing the effectiveness of the treatment.

SUMMARY OF THE INVENTION

A novel formulation for topically delivering benzoyl peroxide used in the treatment of acne has now been developed with significant advantages over preexisting formulations. In particular, it has been found that use of the formulations of the present invention for acne treatment results in effective treatment with reduced irritancy. In accordance with the present invention, porous particles of an inert solid material contain benzoyl peroxide, alone or in solution, retained inside the pores of the particles by capillary forces. The pores are interconnected and open to the particle surface, permitting full diffusion outward of the retained active ingredients. The particles, which are preferably and most conveniently in the form of microspheres, are used either alone as a powder or as a dispersion in a suitable vehicle in a form resembling those of conventional skin preparations such as liniments, gels, lotions or ointments.

In general, the benzoyl peroxide diffuses out of the pores into either the vehicle if one is used or the natural bodily secretions (sebum) present on one's skin at the applied area, in accordance with known principles of the diffusion of one substance through another.

The particles function as controlled delivery systems for the benzoyl peroxide, providing a wide range of advantages over the conventional formulations. Release of the acne treatment substances from the pores of the beads occurs in sustained manner, providing a continuous fresh supply of acne treatment substance to the epidermal area to which the preparation has been applied. Until it is released, the acne treatment substance is essentially unexposed to the atmosphere, and hence contact with oxygen and the risks of oxidation and decomposition are minimal. The formulation remains stable and active for a longer period of time, enhancing its shelf life. In addition, the particles have a dry, smooth, comfortable feel to the skin.

The activity-time curve of the benzoyl peroxide is thus extended and flattened out. The magnitude of the release rate is controlled by the pore volume distribution in the microsphere itself, notably the total pore volume and the average pore diameter. Selection of the values of these parameters according to predetermined standards provides control of the release rate to desired levels. This controlled release rate enhances the continuing treatment of the epidermal area, as sebum is continually produced by the skin. This also reduces the number of times that the skin formulation must be reapplied to the affected area.

The preparations remain active for a longer period of time after having been applied to the skin than conventional formulations, due to the sustained release character. The rate of release can be accelerated at any time thereafter by manual friction to stimulate the outward diffusion of the acne treatment substance. Thus, deeply retained materials may be brought to the surface and made available for their activity at will, many hours after the application of the formulation, without the need for a repeat application.

A further advantage is the ability of the formulation to withstand a higher concentration of acne treatment substance both inside the pores themselves and in the total preparation without the magnitude of side effects previously experienced at these levels. In particular, treatment with the entrapped benzoyl peroxide is as effective as with freely dispersed benzoyl peroxide with reduced skin irritancy.

Surprisingly, the topical compositions of the present invention have been found to be particularly effective in absorbing natural oils, i.e., sebaceous fluids, when applied to the skin for the purpose of acne treatment. When initially applied to the skin, typically as part of a topical formulation, the porous solid particles are substantially or completely loaded with benzoyl peroxide as the active component of the topical composition. It has been found, however, that as the benzoyl peroxide is released from the carrier particles, the natural skin oils are at least partially absorbed. This exchange of benzoyl peroxide for natural skin oils is found to be particularly effective in the treatment of acne where the presence of skin oils is a strong contributing factor.

DETAILED DESCRIPTION OF THE INVENTION AND PREFERRED EMBODIMENTS

Figure 1:
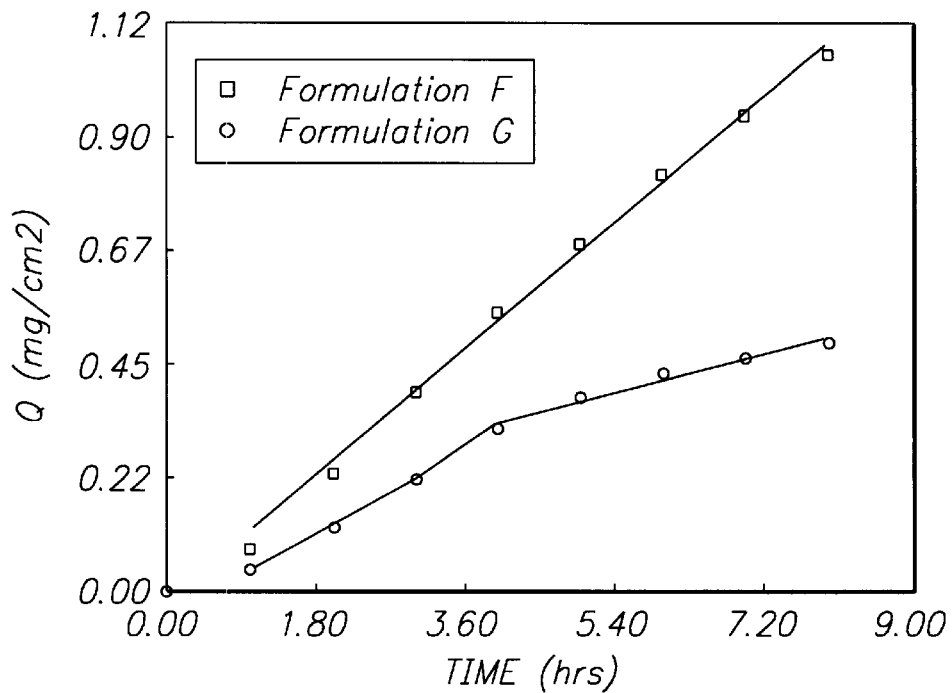
FIG. 1 is a graph illustrating the time release profile of benzoyl peroxide from an entrapped formulation according to the present invention (formulation G) and a non-entrapped formulation (formulation F).

The beads or microspheres used in connection with the present invention are rigid, open-pore, chemically and biologically inert particles with the impregnant held inside the pores by capillary forces. The pores are interconnected and open to the particle surface to an extent that substantially full communication is provided between the internal pore space and the exterior of the particle.

In their most convenient form, the particles are generally spherical in shape, due to the use of suspension polymerization as a preferred method of preparation. While the microspheres may vary widely in size, those falling within the range of about one to about 100 microns in diameter, preferably from about 10 to about 40 microns, will provide the best results. Microspheres within these size ranges are appealing from an aesthetic point of view by imparting a smooth feel to the touch.

The pore dimensions within the spheres may also vary widely, with optimum dimensions depending on the chemical characteristics of the polymers used as well as the diffusive characteristics of the impregnant. Different systems will thus call for different optimum ranges of pore volume distribution to obtain the most desirable properties for the overall formulation. In general, however, best results are obtained with total pore volumes ranging from about 0.01 to about 4.0 cc/g, preferably from about 0.1 to about 2.0; surface areas ranging from about 1 to about 500 $m^2/g$, preferably from about 20 to about 300; and average pore diameters ranging from about 0.001 to about 3.0 micron, preferably from about 0.003 to about 1.0 micron. Following conventional methods of measuring and expressing pore sizes, the pore diameters are calculated from the measurement of the surface area by B.E.T. nitrogen multipoint analysis and from the measurement of the pore volumes by the mercury intrusion method. The calculation is one commonly done by those skilled in the art.

The microspheres are conveniently formed by suspension polymerization in a liquid-liquid system. In general, a solution containing monomers, a polymerization catalyst (if used), and an inert but fully miscible liquid is formed which is immiscible with water. The solution is then suspended in an aqueous solution, which generally contains additives such as surfactants and dispersants to promote the suspension. Once the suspension is established with discrete droplets of the desired size, polymerization is effected (typically by activating the reactants by either increased temperature or irradiation). Once polymerization is complete, the resulting rigid beads are recovered from the suspension. The beads at this point are solid porous structures, the polymer having formed around the inert, water-immiscible liquid, thereby forming the pore network. The liquid has accordingly served as a porogen, or pore-forming agent, and occupies the pores of the formed beads.

Suitable porogens will be liquids meeting the following criteria:

1. They are either fully miscible with the monomer mixture or capable of being made fully miscible by the addition of a minor amount of non-water-miscible solvent;
2. They are immiscible with water, or at most only slightly soluble;
3. They are inert with respect to the monomers, and stable when in contact with any polymerization catalyst used and when subjected to any conditions needed to induce polymerization (such as temperature and radiation); and
4. They are normally liquids or have melting points below the polymerization temperature. Solids can frequently be converted to liquid form by being dissolved in a solvent or by forming eutectic mixtures.

When using this method, the steps must be performed under an inert atmosphere such as nitrogen. If a polymerization catalyst is used, it must be one which does not oxidize the impregnant, if the latter is susceptible to oxidation. Azo catalysts are examples of such catalysts. Also, polymerization temperatures are best held within a moderate range.

The benzoyl peroxide impregnant may be placed inside the pores of preformed dry porous polymer beads. The product is thus prepared in two steps performed in sequence, the polymerization being performed first with a porogen which is then removed and replaced by the benzoyl peroxide in a suitable solvent, typically acetone or isopropanol.

Preferred porogens include hydrocarbons, particularly inert, nonpolar organic solvents. Some of the most convenient examples are alkanes, cycloalkanes, and aromatics. Examples of such solvents are alkanes of 5 to 12 carbon atoms, straight or branched chain, cycloalkanes of 5 to 8 carbon atoms, benzene, and alkyl-substituted benzenes such as toluene and the xylenes. Removal of the porogen may then be effected by solvent extraction, evaporation, or similar conventional operations.

A further advantage of the use of this two-step process is that it permits the removal of unwanted species from the polymerized structures prior to incorporation of the impregnant. Examples of unwanted species include unreacted monomers, residual catalyst, and surface active agents and/or dispersants remaining on the sphere surfaces. A further advantage of this technique is that it permits one to select the amount and type of porogen as a means of controlling the pore characteristics of the finished bead. One is thus no longer bound by the limitations of the impregnant as it affects the structure of the bead itself. This permits partial rather than full filling of the pores with the benzoyl peroxide, and further control over pore size and distribution by selection among swelling and non-swelling porogens.

Extraction of the porogen and its replacement with (i.e., impregnation of the dry bead with) the benzoyl peroxide impregnant in the two-step procedure may be effected in a variety of ways, depending on the chemical nature of the porogen and its behavior in combination with that of the other species present. The beads are first recovered from the suspension by filtration, preferably using vacuum filtration apparatus (such as a Buchner funnel). The beads are then washed with an appropriate solvent to remove organic species not bound to the polymer, including surfactants having deposited on the bead surfaces from the aqueous phase, unreacted monomers and residual catalysts, and the porogen itself. An example of such a solvent is isopropanol, either alone or in aqueous solution. Once washing is complete, the solvent itself is removed by drying, preferably in a vacuum.

In certain cases, an alternative method of extraction may be used, i.e., where the porogen, unreacted monomer and water will form an azeotrope. In these cases, steam distillation is an effective way of extracting porogen from the beads. This again may be followed by drying under vacuum.

Once the beads are rendered dry and free of the substitute porogen and any unwanted organic materials, they are impregnated with the benzoyl peroxide impregnant according to conventional techniques. The most convenient such technique is contact absorption. Solid benzoyl peroxide is dissolved in a solvent, and the resulting solution is absorbed by the beads. The solvent may either be retained in the finished product or removed by conventional means such as evaporation or extraction using a further solvent. Since benzoyl peroxide has limited solubility in most solvents, high contents in the finished bead can be attained by repeated absorptions each followed by solvent removal.

The polymerization process and the various parameters and process conditions involved in the polymerization can be selected and adjusted as a means of controlling the pore characteristics and consequently the capacity and release characteristics of the ultimate product. For example, proper selection of the cross-linking means, the amount and type of cross-linking agent, and the amount and type of porogen are means of attaining such control. Certain polymerization conditions may also be varied to such effect, including temperature, degree of radiation where used, degree of agitation and any other factors affecting the rate of the polymerization reaction.

Cross-linking in the polymer formation is a major means of pore size control. Monomers which may be polymerized to produce cross-linked polymer beads in accordance with the present invention include polyethylenically unsaturated monomers, i.e., those having at least two sites of unsaturation, and monoethylenically unsaturated monomers in combination with one or more polyethylenically unsaturated monomers. In the latter case, the percentage of cross-linking may be controlled by balancing the relative amounts of monoethylenically unsaturated monomer and polyethylenically unsaturated monomer. The polymer beads of the present invention will have greater than 10% cross-linking, preferably from about 10% to about 80% cross-linking, and most preferably from about 20% to about 60% cross-linking. The percentage cross-linking is defined among those skilled in the art as the weight of polyethylenically unsaturated monomer or monomers divided by the total weight of monomer, including both polyethylenically unsaturated and monoethylenically unsaturated monomers.

Monoethylenically unsaturated monomers suitable for preparing polymer beads for the polymer delivery system include ethylene, propylene, isobutylene, diisobutylene, styrene, ethylvinylbenzene, vinylpyridine, vinyltoluene, and dicyclopentadiene; esters of acrylic and methacrylic acid, including the methyl, ethyl, propyl, isopropyl, butyl, sec-butyl, tert-butyl, amyl, hexyl, octyl, ethylhexyl, decyl, dodecyl, cyclohexyl, isobornyl, phenyl, benzyl, alkylphenyl, ethoxymethyl, ethoxyethyl, ethoxypropyl, propoxymethyl, propoxyethyl, propoxypropyl, ethoxyphenyl, ethoxybenzyl, and ethoxycyclohexyl esters; vinyl esters, including vinyl acetate, vinyl propionate, vinyl butyrate and vinyl laurate; vinyl ketones, including vinyl methyl ketone, vinyl ethyl ketone, vinyl isopropyl ketone, and methyl isopropenyl ketone; vinyl ethers, including vinyl methyl ether, vinyl ethyl ether, vinyl propyl ether, and vinyl isobutyl ether; and the like.

Polyethylenically unsaturated monomers which ordinarily act as though they have only one unsaturated group, such as isoprene, butadiene and chloroprene, may be used as part of the monoethylenically unsaturated monomer content.

Polyethylenically unsaturated cross-linking monomers suitable for preparing such polymer beads include diallyl phthalate, ethylene glycol diacrylate, ethylene glycol dimethacrylate, trimethylolpropanetrimethacrylate, divinylsulfone; polyvinyl and polyallyl ethers of ethylene glycol, of glycerol, of pentaerythritol, of diethyleneglycol, of monothio- and dithio-derivatives of glycols, and of resorcinol; divinylketone, divinylsulfide, allyl acrylate, diallyl maleate, diallyl fumarate, diallyl succinate, diallyl carbonate, diallyl malonate, diallyl oxalate, diallyl adipate, diallyl sebacate, divinyl sebacate, diallyl tartrate, diallyl silicate, triallyl tricarballylate, triallyl aconitate, triallyl citrate, triallyl phosphate, divinyl naphthalene, divinylbenzene, trivinylbenzene; alkyldivinylbenzenes having from 1 to 4 alkyl groups of 1 to 2 carbon atoms substituted on the benzene nucleus; alkyltrivinylbenzenes having 1 to 3 alkyl groups of 1 to 2 carbon atoms substituted on the benzene nucleus; trivinylnaphthalenes, and polyvinylanthracenes.

The preferred polymer bead of the present invention will be free from reactive groups which will interact with the porogen and the active ingredient which is ultimately incorporated in the composition. In particular, the beads should be free from reactive amino, hydroxyl, carboxylic, and other reactive functionalities. Such beads will not readily undergo unwanted reactions, will be stable over a wide pH range, will resist moderate oxidation and reduction, will be stable at higher temperatures, will resist attack by moisture, and will have a relatively long shelf life.

Particularly preferred polymer delivery systems of the present invention are formed by the copolymerization of styrene and divinylbenzene, vinyl stearate and divinylbenzene, 4-vinylpyridine and ethylene glycol dimethacrylate, or methylmethacrylate and ethylene glycol dimethacrylate. Usually, the monoethylenically unsaturated monomer will be present at from about 20% to 80% of the monomer mixture, with the polyethylenically unsaturated monomer forming the remainder of the mixture. Particularly preferred is the styrene-divinylbenzene polymeric bead which consists essentially of a hydrocarbon backbone with benzene rings and which is substantially completely free from reactive groups.

Once the microspheres are formed and dried, they are impregnated with the impregnant by contact absorption. In particular, the benzoyl peroxide (which is a solid) impregnant is introduced in the form of a solution in a suitable organic solvent having a relatively low viscosity to facilitate absorption. Benzoyl peroxide is soluble in nearly all organic solvents, slightly soluble in alcohols and slightly soluble in water. It has a melting point of 103° C. to 105° C. and a specific gravity of 1.3340 at 25° C. Examples of such solvents are liquid petrolatum, ether, petroleum ether, alcohols including methanol, ethanol and higher alcohols, aromatics including benzene and toluene, alkanes including pentane, hexane and heptane, ketones including acetone and methyl ethyl ketone, chlorinated hydrocarbons including chloroform, carbon tetrachloride, methylene chloride and ethylene dichloride, acetates including ethyl acetate, and oils including isopropyl myristate, diisopropyl adipate and mineral oil. Preferred are acetone and isopropanol, where solutions of up to about 10% by weight benzoyl peroxide can be obtained.

After absorption of the solution, the solvent can be evaporated or, if desired, retained inside the pores together with the impregnant. Usually, the benzoyl peroxide will be introduced through at least two absorption/evaporation cycles, more usually at least three cycles, and frequently four or more. In this way, compositions of up to 65% benzoyl peroxide (based on total dry weight) can be obtained usually being from 10% to 40% by weight.

Other formulating materials, such as carriers or adjuvants such as fragrances, preservatives, antioxidants, and emollients can also be present, and will be incorporated into and onto the beads together with the impregnants and any other materials present. Optionally, other acne treatment substances, such as salicylic acid and salicylates can be incorporated in the compositions.

The benzoyl peroxide impregnant, whether it be pure (solid) active ingredient, a mixture of active ingredients, or a solution of active ingredient, will generally comprise between approximately 5% and approximately 65% of the total weight of the impregnated beads, usually being from 10% to 40% of the total weight.

The benzoyl peroxide impregnated beads of the present invention will be used for topical treatment of regions of the skin suffering from acne lesions and may be used alone or more commonly in the form of fluid compositions or preparations similar to those commonly used for skin treatment, for example: gels, creams, lotions, ointments, sprays, powders, or oils. Appropriate vehicles for particular areas or methods of application will be readily apparent to those skilled in the art. When liquid vehicles are used (such as gels, creams, lotions, ointments or oils) and the impregnant is a solution of an active ingredient in a solvent, the solvent and vehicle must be immiscible so that outward diffusion of the active ingredient will not be accelerated by mutual diffusion between the solvent and vehicle. Appropriate combinations will therefore include the combination of a polar solvent and a nonpolar vehicle, and the combination of a nonpolar solvent and a polar vehicle. More commonly, the benzoyl peroxide will be present as a solid within the bead at relatively high concentrations. Release may be effected either by extraction mediated by the liquid carrier or, more usually, by extraction mediated by the user's sebum (skin secretions of the sebaceous glands).

The following examples relate to preparation and utility of the acne treatment formulations of the present invention. The examples are offered solely for purposes of illustration, and are intended neither to limit nor define the invention in any manner. All parts and percentages are by weight, unless otherwise stated.

EXPERIMENTAL

Example One

A 2000 ml four-necked reaction flask equipped with a motorized stirrer, reflux condenser, thermometer, and nitrogen inlet was purged with nitrogen. 800 parts of deionized water, 6.4 parts of gum arabic and 6.4 parts of a sodium-based lignosulfonate available from Reed Lignins, Inc., under the trademark Marasperse N-22, were charged to the reaction flask. The mixture was heated, with stirring, in an oil bath at about 50° C. until the dispersants (gum arabic and lignosulfate) dissolved to form an aqueous phase.

To this mixture there was then added a freshly prepared solution of 102.3 parts of styrene (99.8% purity), 85.6 parts of commercial divinylbenzene (55.6% divinyl benzene, 42.3% ethylvinylbenzene), 5.3 parts of benzoyl peroxide (70% active ingredient and 30% water), and 130 parts of heptane. The aqueous phase and organic solution were agitated by stirring at a rate adjusted to give a plurality of droplets having an average droplet diameter of about 10–60 microns, as determined by visual observation of a sample of the droplets with an optical microscope (400×) with the droplets being stabilized by the dispersants. This rate is approximately 1200 rpm. The reaction mixture was then heated to about 80° C. and maintained at that temperature for about 20 hours, at the previously adjusted stirring rate, to form porous beads of cross-linked styrene/divinylbenzene copolymer having heptane entrapped within the network of pores. The mixture was then cooled, diluted with 200 parts of water, and the porous polymeric beads were removed from the reaction flask by filtration. The filtered beads were washed initially three times with one liter portions of deionized water to remove the dispersants, followed by three washes with 0.6 liter portions of isopropanol: acetone mixture (7:3, respectively, by weight) to remove any residual, unreacted monomer and the heptane used as the porogen during polymerization. The beads were then dried in an oven at 80°–100° C. for eight hours.

The average particle diameter of these beads was 25 microns, as measured by a Sedimentation Micromeritics Microsizer 5300, an instrument available from Micromeritics Instrument Company, Norcross, Ga. The particle diameter determination method is described in detail in the "Microsizer 5300 Particle Size Analyzer Instruction Manual" (1984) associated with the instrument.

The calculated or theoretical cross-linking density of the purified beads is 25%. This density is calculated by multiplying the weight of divinylbenzene (85.6 parts) by the purity of the divinylbenzene (55.6%) to get the actual weight of pure divinylbenzene which is then divided by the total weight of monomer (85.6 parts+102.3 parts) and multiplied by 100.

The surface area of a sample of the purified beads was determined by the B.E.T. nitrogen multipoint analysis to be 91.2 m$^2$/g while the pore volume was determined by the mercury intrusion method to be 1.0 cc/g. The B.E.T. method is described in detail in Brunauer et al. (1938) J. Am. Chem. Soc., 60: 309–316. The mercury intrusion method is described in detail in *Advanced Experimental Techniques in Powder Metallurgy*, pages 225–252, (Plenum Press, 1970).

Examples Two and Three

By repeating the procedure of Example One in every essential detail, except for the weights of monomers and porogen employed, porous cross-linked polymer beads were obtained having the following characteristics listed in Table 1:

TABLE 1

| Example | Ratio of Parts Styrene/Divinyl-Benzene/Porogen | Calculated Cross-Inking Density, % | Avg. Particle Diam, μm | Surface Area m$^2$/g | Pore Volume ml/g |
|---|---|---|---|---|---|
| 2 | 89/100/180 (porogen = mineral oil) | 29 | 25 | 75 | 1.36 |
| 3 | 85.6/102.3/188 (porogen = toluene) | 30 | 25 | 1.8 | 0.04 |

Example Four

A 10 part portion of the macroporous cross-linked polymer beads prepared as described in each of Examples One–Three above was mixed at room temperature with 16 parts of a 12.5% solution of benzoyl peroxide in acetone, and the resulting suspensions were hand-stirred for a few minutes. The thus-obtained homogeneous wet powders were washed three times with 30 ml portions of deionized water in a funnel, then air dried at room temperature for 20 hours. The benzoyl peroxide contents entrapped within these beads' macropores as determined by titration with iodine in isopropanol and based on the total weight of beads and entrapped benzoyl peroxide, were as follows:

TABLE 2

| Beads of Example | Wt. of Water, % | Wt. of Benzoyl Peroxide, % |
|---|---|---|
| 1 | 1 | 12.2 |
| 2 | 1 | 12.1 |
| 3 | 8 | 9.6 |

Example Five

Two 10 part portions of the macroporous cross-linked polymer beads prepared as described in Example One above were mixed at room temperature with a 14 part portion of a 12.5% solution of benzoyl peroxide in acetone and a 10 part portion of a 20% solution of salicylic acid in acetone, respectively. The resulting wet powders were hand-stirred until homogeneous, then air-dried at room temperature for 20 hours. Their respective contents of benzoyl peroxide and salicylic acid, as determined by titration with iodine and dilute aqueous sodium hydroxide, respectively, and based on the total weight of beads and entrapped benzoyl peroxide and salicylic acid, were:

| | |
|---|---|
| Benzoyl peroxide | 11.3% |
| Salicylic acid | 16% |

The two lots of beads were then commingled to provide a therapeutic delivery system for topically applying benzoyl peroxide and salicylic acid together to the skin.

Example Six

Skin absorption of benzoyl peroxide (BPO) from a topical lotion containing freely dispersed drug was compared with that from the same lotion in which the drug was entrapped in a controlled-release styrene-divinylbenzene polymer system. In an in vitro diffusion system, statistically significant (p=0.01) differences were found in the content of benzoyl peroxide in excised human skin and in percutaneous absorption. In vivo, significantly (p=0.002) less benzoyl peroxide was absorbed through rhesus monkey skin from the polymeric system. This controlled release of benzoyl peroxide to skin can alter the dose relation that exists between efficacy and skin irritation. Corresponding studies showed reduced skin irritation in cumulative irritancy studies in rabbits and human beings, whereas in vivo human antimicrobial efficacy studies showed that application of the formulations containing entrapped benzoyl peroxide significantly reduced counts of *Propionibacterium acnes* (p<0.001) and aerobic bacteria (p<0.001) and the free fatty acid/triglyceride ratio in skin lipids. These findings demonstrate that controlled topical delivery of benzoyl peroxide can enhance safety without sacrificing efficacy.

1. Preparation of BPO formulations

Tritium BPO (97% chemical and radiochemical purity), was formulated as a 5% lotion with the tritium BPO freely dispersed (formulation A) or entrapped in a styrene-divinylbenzene delivery system (25% cross-linking) (formulation B) and with a mean particle size of 25 μm (range 5 to 50 μm).

Five formulations, formulation C (simple oil-in-water emulsion vehicle [SOWE]), formulation D (2.5% free BPO in SOWE), formulation E (2.5% entrapped BPO in SOWE), formulation F (5% free BPO in SOWE), and formulation G (5.0% entrapped BPO in SOWE), were prepared for the rabbit skin irritancy and the antimicrobial efficacy studies. The % designation represents the total weight of BPO per 100 gm of final formulation.

For cosmetic reasons the vehicle composition was somewhat modified, and conventional non-entrapped BPO formulations containing 2.5% (formulation H) and 10.0% (formulation J) entrapped active ingredient were prepared and tested both in vitro for release rates and in vivo for human irritancy and antimicrobial efficacy. In these irritancy tests, commercial products containing BPO (formulation K, with 2.5% BPO, and formulation L, with 10.0% BPO) were used for comparison.

2. BPO release rates from formulations

Silastic® membranes (#500-1) were mounted in static diffusion cells (Franz (1975) J. Invest. Dermatol. 64: 190–195) and the membrane surfaces dosed with 5% BPO lotion containing BPO either freely dispersed (formulation F) or entrapped in the polymer system (formulation G) at a rate of 5 µl (5 mg) of formulation/cm². The formulations containing 2.5% and 10% BPO (formulations H and J) were also tested and compared with commercial products containing similar drug concentrations (formulations K and L). Receptor fluid composed of distilled water/acetone (1:1) was added to the cell and maintained at 25° C. Because of the exceedingly low solubility of BPO in either water of normal saline solution, a water/acetone mixture was selected as receptor fluid to provide adequate "sink" conditions after preliminary experiments showed no interactions of this mixture with either the membrane or the mixtures placed on the "donor" side. Drug flux through the membrane was determined by periodically withdrawing the receptor phase and analyzing for permeate content by high-performance liquid chromatography (HPLC). Analyses were performed on a Perkin-Elmer HPLC system (Perkin-Elmer Corp., Norwalk, Conn.) fitted with a binary pump (model 250), autosampler (model ISS100), LC-95 spectrophotometer, and Nelson 2600 data station. A 5 µm ultrasphere reversed-phase column in octadecylsilane form (4.6 mm inner diameter×25 cm length) was used. The mobile phase was methanol/water (75:25), and the flow rate was set at 1.2 ml/min. The spectrophotometer was set at 254 nm and injection volume was 10 µl. The retention times were 8.0 minutes for BPO and 5.2 minutes for benzophenone (internal standard). The results were reported as an average of two determinations.

3. In vitro skin diffusion system

Skin was excised from human thigh with a dermatome set at 0.5 mm thickness from (1) a 58-year old black man, (2) a 40-year old black man, and (3) a 20-year old white woman. Specimens were obtained shortly after death, stored refrigerated, and used within 7 to 10 days. Previous studies (Nacht et al. (1981) J. Am. Acad. Dermatol. 4: 31–37) have shown that under these conditions the intrinsic skin permeability is not altered. In addition, when human skin specimens are used within this time, BPO during skin absorption is metabolized to benzoic acid and accumulated as such in the receptor fluid. Three or four replicates per human skin source were used, giving a total of 10 replicates. A 5 µl volume of lotion containing 0.9 µCi(A) or 1.2 µCi(B) was spread over 1 cm² area of skin mounted on the diffusion cell.

The diffusion cells were made of glass with flow-through design (Reifenrath et al. (1985) In: *Percutaneous Absorption: Mechanisms—Methodology/Drug Delivery*, Bronaugh R, Maibach HI, eds. New York, Marcel Dekker, pp. 305–335). Buffered saline receptor fluid was maintained at 37° C. and pumped at one reservoir volume (3 ml) per hour. Hourly reservoir samples were accumulated for 24 hours. After 24 hours of application time, tritium content was determined in the accumulated reservoir fluid, skin surface washes and in the skin itself. The receptor phase samples from the permeation cells were analyzed for permeant content by scintillation counting (liquid scintillation counter, model 4640, Packard Instrument Co., Meriden, Conn.) within 24 hours after sampling. At the end of the monitoring period the skin surface was washed with soap (20% Ivory liquid) followed by two water rinses, and the wash solutions were analyzed for residual drug content by scintillation counting. The skin membrane itself was physically separated by heat (Shah et al. (1987) Pharm. Res. 4: 265–267) into epidermis and dermis, and each portion was completely solubilized with a tissue solubilizer (Soluene, Packard Instrument Co.). Aliquots of these homogenates were analyzed for drug content by scintillation counting. A mass comparison between the two test formulations was established for the amount of drug remaining on the skin surface, that which was retained within the skin, and that which permeated into the receptor phase. Material balance for BPO was determined for both formulations (Wester (1989) In: *Percutaneous Absorption: Mechanisms—Methodology/Drug Delivery*, Bronaugh R, Maibach HI, eds. New York, Marcel Dekker, pp. 653–659). Statistical analyses were done by means of StatPlus software (Human Systems Dynamics, Northridge, Calif.) and an Apple IIe computer.

4. In vivo percutaneous absorption

Female rhesus monkeys (n=4) were placed in metabolic chairs, and each topical dose was applied to a premeasured area of abdominal skin. A 75 µl volume containing 3.4 µCi(A) or 3.3 µCi(B) was spread over a 12 cm² area of abdominal skin. The monkeys had free access to food and water but were restricted from touching their abdominal area by barrier plates. Urine was collected in a pan under the metabolic chair. A barrier plate was placed between the dose application skin area on the monkey and the urine collection pan below the monkey to prevent contamination from applied material that might fall off the skin because of skin desquamation. Urine was collected for 24 hours in the metabolic chair. The skin site of application was washed with soap (20% Ivory liquid) and two water rinses, and the monkeys transferred to metabolic cages for continued urine collection during the next 6 days (Wester et al. (1975) Toxicol. Appl. Pharmacol. 32: 394–398). Aliquots of urine were analyzed for tritium content by scintillation counting. Statistical analyses were done as described earlier.

5. Cumulative skin irritancy

In rabbits. Two groups of New Zealand strain rabbits (six animals/group), male or female, weighing between 2 and 4 kg, were used. Group 1 received formulations C, D, and E and group 2 received formulations C, F, and G. The hair from the backs of the animals was clipped 24 hours before the first test material application; 0.025 ml of each formulation was applied over a previously marked 2 cm² area for 21 days, 5 days a week. Irritancy observations were recorded daily with the following scale: grade 0, no skin reaction; grade 0.5, barely perceptible, spotty erythema; grade 1.0, mild, even erythema covering the whole area of application; grade 2.0, intense erythema with clearly defined edge; grade 3.0 intense erythema plus edema, raised edge; grade 4.0, intense erythema, edema, and bullae; grade 5.0, necrosis.

In human beings. Formulations H and J, containing 2.5% and 10.0% BPO, respectively, were tested on the backs of human volunteers in a 14-day cumulative irritancy open-patch test (Nacht (1986) Cosmetics & Toiletries 101: 47–55). A panel of 25 volunteers was enrolled by a commercial testing laboratory (Derma-Test Laboratories, Inc., Long Island City, N.Y.). In this study, the test materials were applied to the subjects' backs daily, Monday through Friday, for 2 weeks. The dosage was 150 µl per patch. Patches were made of nonwoven cotton cloth (Webril, Curity) 20 mm in diameter, covered with paper adhesive tape (Scanpor, Norgeplaster, Oslo, Norway), and held in place with occlusive plastic tape (Blenderm Surgical Tape, 3M Co., St. Paul, Minn.). Irritancy was scored daily, on a blind basis, according to the following scale: 0, no visible reaction; 1, mild erythema; 2, moderate erythema with edema; 3, intense erythema with edema; 4, intense erythema, and vesicular erosion. The results were expressed as (1) the percentage of the total subjects showing a response and (2) the cumulative response index (CRI), calculated as the sum of the mean daily scores of all the subjects tested.

6. In vivo antimicrobial efficacy

Formulation G (5.0% entrapped BPO in SOWE) was initially studied. Twelve healthy male and female informed volunteers older than 18 years of age were selected. The subjects were free of any cutaneous or internal diseases, and each had no known allergies or sensitivities to topical products and specifically to anti-acne preparations.

Subjects were screened bacteriologically to ascertain that they had *P. acnes* counts equal to or greater than 100,000 organisms per square centimeter. The formulation was applied twice daily, 5 days a week for 2 weeks under the supervision of the investigator (at Ivy Laboratories, Philadelphia, Pa.). Each subject was instructed to avoid the use of any other topical product on the face during the study period and against the use of medicated soaps. Quantitative bacteriologic cultures were obtained according to the method of Williamson and Kligman (1965) J. Invest. Dermatol. 45: 498–503 from the forehead before starting and again on days 7 and 14. Culture samples were obtained 24 hours after the last application of BPO and the culture fluids were monitored for drug carryover.

Subsequently, formulations H and J containing entrapped BPO at 2.5% and 10.0% concentrations were also tested for antimicrobial efficacy against *P. acnes*. The reduction in the number of organisms recovered from the skin surface and the changes in the free fatty acids/triglyceride ratio (FFA/TG) in skin surface lipids were measured.

7. Results

Figure 2:
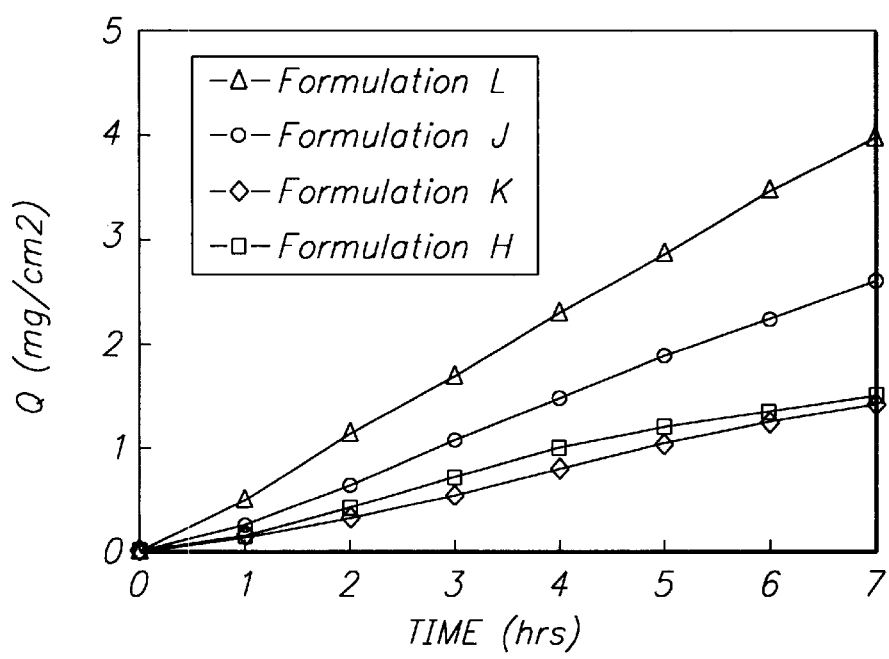
FIG. 2 is a graph comparing the time release profiles of benzoyl peroxide from entrapped formulations (J and H) according to the present invention with non-entrapped formulations (K and L).

The cumulative release of BPO from formulations F and G through the Silastic membrane is shown in FIG. 1. Apparent "zero order" release of BPO from these formulations is observed. This result is expected because, as a result of the very low solubility of this drug in the formulation, maximal thermodynamic activity is maintained in the donor side throughout the experiment. When freely dispersed, BPO steady-state flux was 0.09 mg/cm$^2$/hr. When entrapped, the initial flux was practically identical (0.1 mg/cm$^2$/hr). This similarity most likely reflects the small amount of BPO adsorbed onto the outside of the polymeric spheres. This hypothesis was confirmed by observing the polymeric powder under the microscope with polarized light; a small amount of crystalline refringent material could be detected. When this pool of free BPO was depleted, the flux changed abruptly to 0.04 mg/cm$^2$/hr and remained at this rate for the next 30 hours. This flux represents the release of entrapped drug from the macroporous polymer system. The inflection point indicates initiation of controlled release. FIG. 2 represents the release profiles of BPO from formulations H and J compared with their commercial counterparts (formulations K and L).

Table 3 presents the results for the in vitro percutaneous absorption of BPO through human skin. There was a statistically significant difference (p=0.01) between formulations A and B in the percent of applied dose retained in the skin and accumulated in the receptor fluid. This difference supports the concept of controlled release of the BPO from the polymer delivery system into and through the skin. In both cases most of the applied dose was recovered in the surface washes. Most of the tritium content within the skin was in the epidermis, and total material accountability for both systems was good.

TABLE 3

In vitro percutaneous absorption of benzoyl peroxide in human skin

| | % Applied dose[1] | | |
|---|---|---|---|
| Parameter* | Formulation A (freely dispersed) | Formulation B (entrapped) | Statistical Comparison[2] |
| Skin | 6.1 ± 4.4 | 1.4 ± 0.8 | p = 0.01 |
| Epidermis | 5.2 ± 4.1 | 1.1 ± 0.7 | p = 0.02 |
| Dermis | 0.4 ± 0.4 | 0.1 ± 0.1 | p > 0.05 (NS) |
| Skin edge | 0.6 ± 0.7 | 0.2 ± 0.3 | p > 0.05 (NS) |
| Receptor fluid | 17.1 ± 15.7 | 3.5 ± 3.4 | p < 0.05 |
| Surface wash | 85.6 ± 29.0 | 83.2 ± 19.9 | p > 0.05 (NS) |
| Total | 108.9 ± 22.3 | 88.1 ± 18.4 | p > 0.05 (NS) |

NS = Not statistically significant; skin edge, edge where system is clamped together.
*N = 10 for each parameter.
[1] = Data presented as mean ± SD.
[2] = Student's test.

Figure 3:
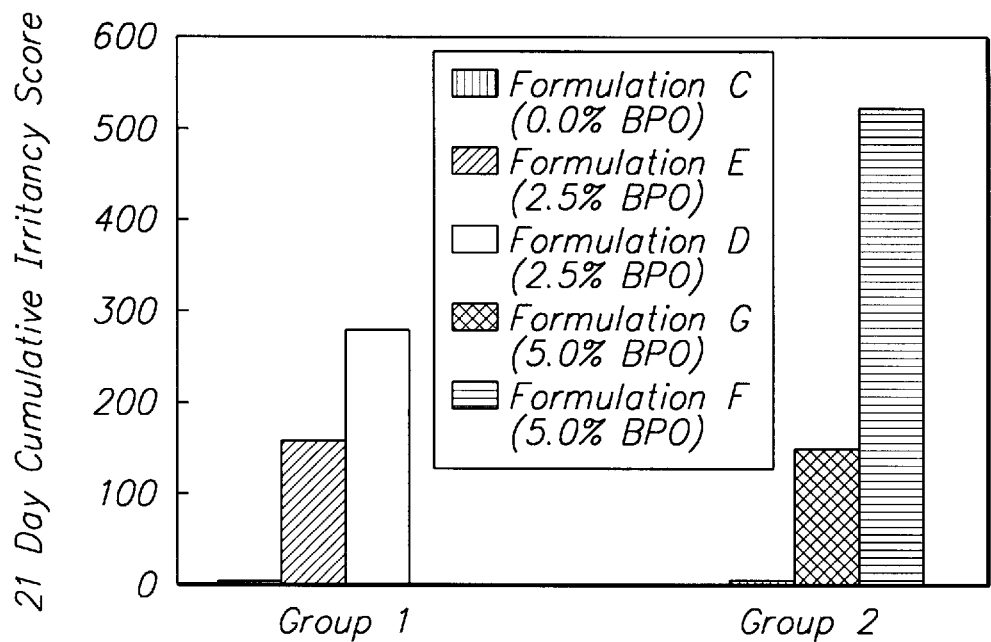
FIG. 3 is a chart comparing cumulative 21-day irritancy scores for various benzoyl peroxide formulations in rabbits. Results are the sum of total irritancy scores in each group. Six animals per group were used.

Table 4 reflects the in vivo percutaneous absorption of BPO in the rhesus monkey. Absorption from formulation A, with BPO freely dispersed in the lotion, was 14.8%±1.5%. Absorption of BPO entrapped in the macroporous polymer, formulation B, was significantly (p=0.002) less at 8.6%±0.8%. For both formulations, most of the tritium was excreted in the first 24-hour urine sample. FIG. 3 presents the 21-day cumulative irritancy scores of the various formulations tested in rabbits. Entrapping BPO in a controlled-release polymer system significantly reduced the drug skin irritation potential both at 2.5% (p<0.001) and at 5.0% (p<0.001) BPO concentrations in the formulations.

TABLE 4

In vivo percutaneous absorption of benzoyl peroxide in the rhesus monkey

| | % Dose absorbed | |
|---|---|---|
| Monkey | Formulation A (freely dispersed) | Formulation B (entrapped) |
| 1 | 16.7 | 8.5 |
| 2 | 15.3 | 9.7 |
| 3 | 13.9 | 8.4 |
| 4 | 13.4 | 7.7 |
| Mean ± SD | 14.8* ± 1.5 | 8.6* ± 0.8 |

*p = 0.002

The results from the human cumulative irritancy test are presented in Table 5. At each BPO concentration, the formulation containing entrapped BPO was significantly less (p<0.05) irritating than its commercial counterpart.

TABLE 5

14-Day cumulative irritancy in humans

| Formulation | % Total subjects with positive response | Cumulative response index* |
|---|---|---|
| I. 2.5% BPO | | |
| Commercial product (K) | 36 | 1.04 (1) |
| Entrapped BPO (H) | 12 | 0.24 (2) |
| Vehicle | 0 | 0.0 (3) |

TABLE 5-continued

14-Day cumulative irritancy in humans

| Formulation | % Total subjects with positive response | Cumulative response index* |
|---|---|---|
| II. 10% BPO | | |
| Commercial product (L) | 52 | 2.59 (4) |
| Entrapped BPO (J) | 24 | 1.64 (5) |
| Vehicle | 0 | 0.0 (6) |

*Duncan's Multiple Range test showed significant difference ($p < 0.05$) between 1 and 2, 1 and 3, and 4 and 5, 4 and 6, 5 and 6; but no significant difference ($p > 0.05$) between 2 and 3.

Figure 4:
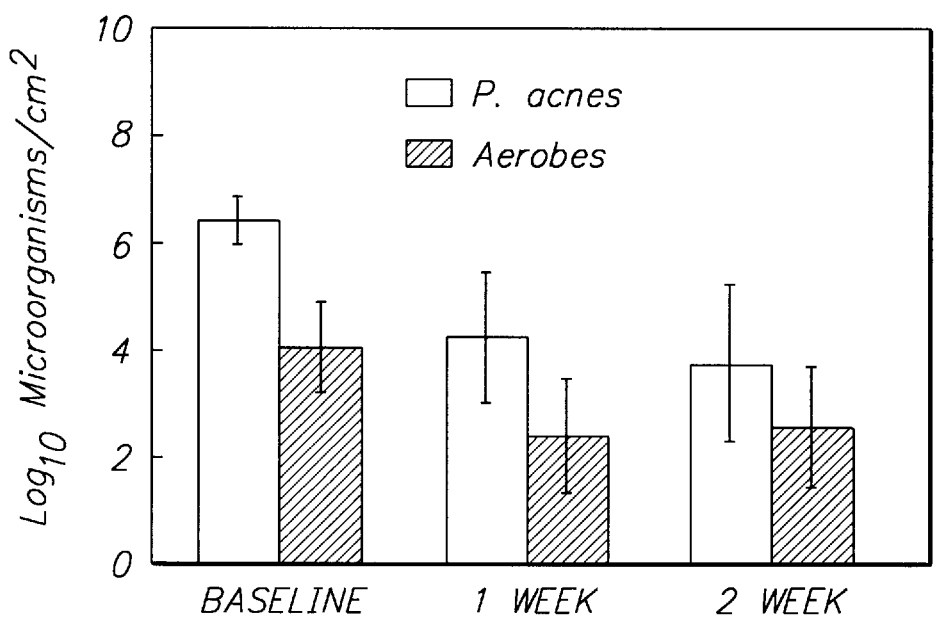
FIG. 4 is a chart illustrating the reduction in *P. acnes* and aerobe counts after treatment with a formulation according to the present invention.

All the test samples (scrubs) obtained in vivo from the human volunteers at days 0, 7, and 14 were cultured for *P. acnes* and for aerobic bacteria. The number of *P. acnes*, expressed as $\log_{10}$ per $cm^2$ at baseline and on days 7 and 14 of treatment, are shown in FIG. 4 for the initial test. The mean *P. acnes* counts were significantly ($p<0.001$) reduced over the baseline at both 7 and 14 days after treatment, with an average reduction of at least two orders of magnitude in the counts. FIG. 4 also shows approximately two orders of magnitude reduction in the aerobic bacteria ($p<0.001$).

When the reformulated products (formulations H and J) containing 2.5% and 10.0% BPO were tested for antimicrobial efficacy, significant reductions ($p<0.05$) were observed both in the number of *P. acnes* and in the FFA/TG ratio in skin surface lipids (Table 6). No significant differences between treatments were detected at any time point.

TABLE 6

In vivo antimicrobial efficacy of formulations containing 2.5% and 10% entrapped BPO

| Formulation | P. acnes count* ($\log_{10}$ bacteria/$cm^2$) | | | FFA/TG ratio* | | |
|---|---|---|---|---|---|---|
| | Baseline | Week 2 | Week 4 | Baseline | Week 2 | Week 4 |
| 2.5% BPO (H) | 6.04 (±0.65) | 2.75† (±1.82) | 2.25† (±2.01) | 0.74 (±0.28) | 0.45† (±0.19) | 0.32† (±0.23) |
| 10% BPO (J) | 5.58 (±0.51) | 3.04† (±1.89) | 1.92† ±1.85) | 0.71 (±0.19) | 0.53† (±0.17) | 0.31† (±0.11) |

*Data presented as mean ± SD.
†Difference between this value and baseline is significant at the 95% confidence level (Dunnett's *t* tests).

Discussion

Because BPO pharmacologic activity is a consequence of its ability to penetrate into the skin preferentially through the follicular openings, a controlled-release topical delivery system might reduce the percutaneous absorption of BPO without affecting its intrafollicular penetration, thereby reducing the irritancy of the drug without sacrificing efficacy.

Therefore, we compared the skin absorption of BPO from topical formulations in which the drug was either freely dispersed or was entrapped in a controlled-release macroporous polymer delivery system. Statistically significant differences were found between these formulations in BPO content in the skin, receptor fluid accumulation, and in in vivo skin penetration in the rhesus monkey. Release studies of BPO through artificial Silastic membranes and through excised human skin indicate a controlled release of BPO from the macroporous polymer system into and through the skin. Corresponding studies of rabbit skin irritation with freely dispersed and entrapped BPO showed reduced skin irritation with the entrapped/controlled-release system. This effect was further confirmed when formulations containing entrapped BPO at 2.5% and 10.0% concentrations were tested in comparison to their commercial counterparts for cumulative irritancy in human beings. Here again the controlled-release formulation demonstrated a significantly lower irritancy potential than the conventional vehicles. However, when the experimental formulations were evaluated for antimicrobial activity in vivo, their efficacy was unexpectedly in line with that of conventional products. These results demonstrate that controlled release can provide the means for dissociating the dose relation between efficacy and irritation for BPO.

Example Seven

A clinical study was conducted to evaluate the relative efficacy of entrapped and non-entrapped benzoyl peroxide formulations with concentrations of 2.5%, 5%, or 10% benzoyl peroxide in a cream vehicle. The study was conducted on 175 subjects, and vehicles with the particular carriers but no benzoyl peroxide (placebo) were used as a negative control. As a positive control, a commercial non-entrapped BPO product with 10% benzoyl peroxide, was used. The study was 12 weeks in duration, and at appropriate intervals the investigator counted and recorded the non-inflammatory lesions (open and close comedones) and the inflammatory lesions (papules and pustules). The study was conducted on a double blind fashion. Namely, neither the investigator nor the subjects knew the identity of the product being used.

Figure 5:
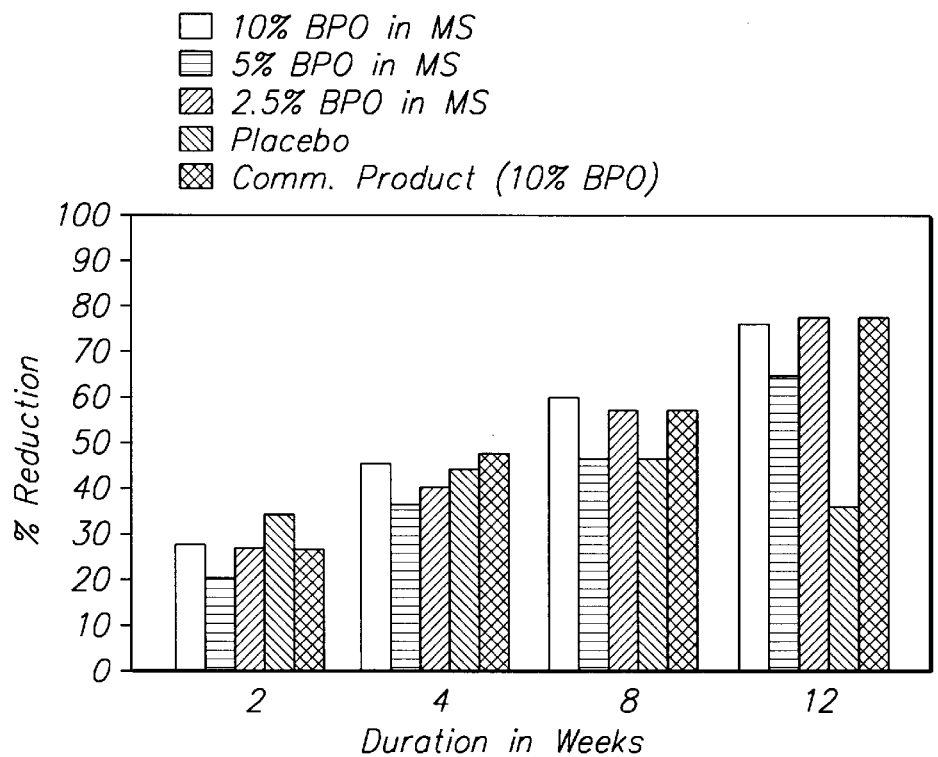
FIGS. 5 and 6 are charts which compare the effectiveness of entrapped and free benzoyl peroxide formulations in treating inflammatory and non-inflammatory lesions caused by acne.
Figure 6:
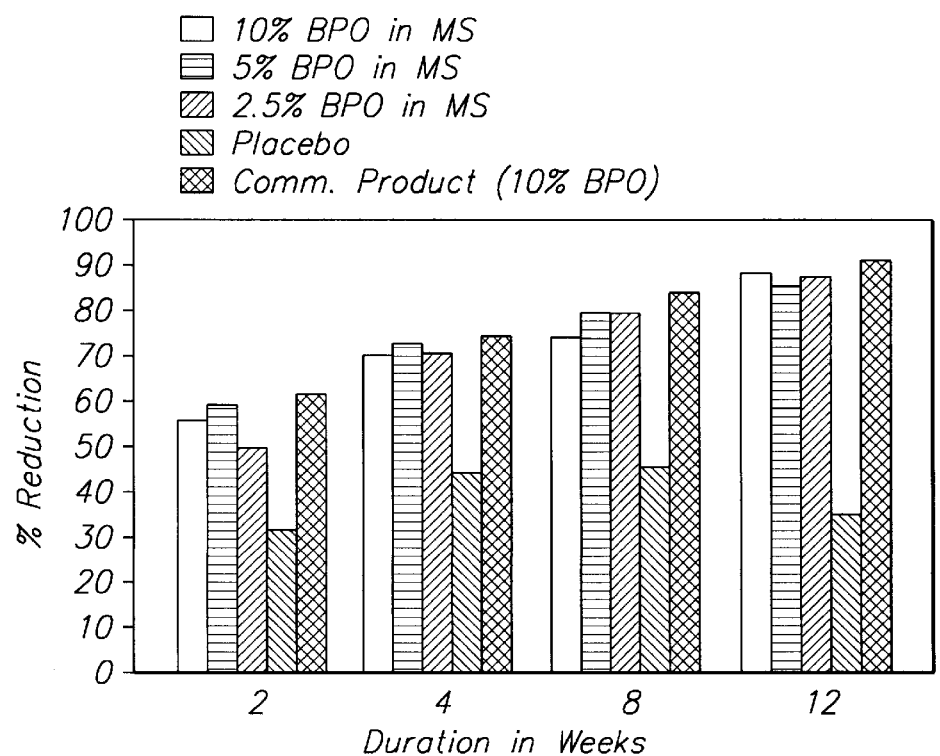

The results obtained are presented in graphical form in FIGS. 5 and 6. As can be seen, there was a gradual and progressive reduction in the total number of non-inflammatory lesions in all groups, except in the placebo. A similar reduction was observed in the inflammatory lesions. Surprisingly, it was found that all the formulations containing benzoyl peroxide in the particulate carriers were equally effective and as effective as the commercial product positive control. This is to say that a 2.5% benzoyl peroxide in microsponges was as effective as the non-entrapped commercial product (10% benzoyl peroxide). Based on the results obtained in previous irritancy tests (summarized in Table 5 above), the 2.5% BPO formulation in microsponges produced a cumulative response index (CRI) of 0.24, while the 10% BPO commercial product had an irritancy of 2.59; namely, ten times larger than a microsponge formulation with equal clinical efficacy. Thus, the controlled release particulate delivery system of the present invention can provide efficacy equal to that of a non-entrapped formulation containing four times the benzoyl peroxide with one-tenth of the irritancy.

The foregoing description is directed primarily to preferred embodiments and practices of the present invention. It will be readily apparent to those skilled in the art that further changes and modifications in the actual implementation of the concepts described herein can be made without departing from the spirit and scope of the invention as defined by the following claims.

What is claimed is:

1. A topical composition for the treatment of acne, the composition comprising:
   (a) solid particles composed of a cross-linked copolymer of monoethylenically unsaturated monomers and polyethylenically unsaturated monomers and having a cross-linking density from 20% to 80%, wherein said particles contain a continuous noncollapsible network of pores open to the exterior of said particles, are substantially spherical in shape, and have an average diameter of about 1 micron to about 100 microns, a total pore volume of about 0.01 cc/g to about 4.0 cc/g, a surface area of about 1 $m^2/g$ to about 500 $m^2/g$, and an average pore diameter of about 0.001 micron to about 3.0 microns, and (b) an impregnant comprising benzoyl peroxide retained inside said pores in an amount effective to treat acne when applied to the skin, wherein retention of said benzoyl peroxide inside said pores reduces irritancy of the composition when compared to application of the same amount of free benzoyl peroxide without loss of acne treatment activity.

2. A topical composition in accordance with claim 1 in which said benzoyl peroxide is retained inside said pores as a solid.

3. A topical composition in accordance with claim 1 in which said benzoyl peroxide is retained inside said pores in a solvent selected from the group consisting of ethers, esters, alcohols, aromatics, and alkanes.

4. A topical composition in accordance with claim 1 in which said solid particles have an average diameter of about 10 microns to about 40 microns, a total pore volume of about 0.1 cc/g to about 2.0 cc/g, a surface area of about 20 $m^2/g$ to about 200 $m^2/g$, and an average pore diameter of about 0.003 micron to about 1.0 micron.

5. A topical composition in accordance with claim 1 in which said solid particles are composed of a cross-linked copolymer of styrene and divinylbenzene.

6. A topical composition in accordance with claim 1 in which said solid particles are composed of a cross-linked copolymer of methyl methacrylate and ethylene glycol dimethacrylate.

7. A topical composition in accordance with claim 1 in which said solid particles are composed of a cross-linked copolymer of 4-vinylpyridine and ethylene glycol dimethacrylate.

8. A topical composition in accordance with claim 1 in which said solid particles are combined with a vehicle to form a composition selected from the group consisting of fluid, semi-solid, and solid compositions.

9. A topical composition in accordance with claim 1 in which said impregnant comprises about 10 to about 40% by weight of the total weight of said solid particles and said impregnant.

10. A topical composition in accordance with claim 1 in which said impregnant further comprises salicylic acid.

11. A method for the treatment of acne, the method comprising applying to the skin a topical composition comprising:

(a) solid particles composed of a cross-linked copolymer of monoethylenically unsaturated monomers and polyethylenically unsaturated monomers and having a cross-linking density from 20% to 80%, wherein said particles contain a continuous noncollapsible network of pores open to the exterior of said particles, are substantially spherical in shape and have an average diameter of about 1 micron to about 100 microns, a total pore volume of about 0.01 cc/g to about 4.0 cc/g, a surface area of about 1 $m^2/g$ to about 500 $m^2/g$, and an average pore diameter of about 0.001 micron to about 3.0 microns, and (b) an impregnant comprising benzoyl peroxide retained inside said pores in an amount effective to treat acne when applied to the skin, wherein retention of said benzoyl peroxide inside said pores reduces irritancy of the composition when compared to application of the same amount of free benzoyl peroxide without loss of acne treatment activity.

12. A method in accordance with claim 11 in which said benzoyl peroxide is retained inside said pores as a solid.

13. A method in accordance with claim 11 in which said benzoyl peroxide is retained inside said pores in a solvent selected from the group consisting of ethers, esters, alcohols, aromatics, and alkanes.

14. A method in accordance with claim 11 in which said solid particles have an average diameter of about 10 microns to about 40 microns, a total pore volume of about 0.1 cc/g to about 2.0 cc/g, a surface area of about 20 $m^2/g$ to about 200 $m^2/g$, and an average pore diameter of about 0.003 micron to about 1.0 micron.

15. A method in accordance with claim 11 in which said solid particles are composed of a cross-linked copolymer of styrene and divinylbenzene.

16. A method in accordance with claim 11 in which said solid particles are composed of a cross-linked copolymer of methyl methacrylate and ethylene glycol dimethacrylate.

17. A method in accordance with claim 11 in which said solid particles are composed of a cross-linked copolymer of 4-vinylpyridine and ethylene glycol dimethacrylate.

18. A method in accordance with claim 11 in which said solid particles are combined with a vehicle to form a composition selected from the group consisting of fluid, semi-solid, and solid compositions.

19. A method in accordance with claim 11 in which said impregnant comprises about 10% to about 40% by weight of the total weight of said solid particles and said impregnant.

20. A method in accordance with claim 11 in which said impregnant further comprises salicylic acid.

* * * * *